United States Patent [19]

McCutchan et al.

[11] Patent Number: 4,707,445

[45] Date of Patent: Nov. 17, 1987

[54] INTACT GENE AND METHOD OF EXCISING AND CLONING SAME

[75] Inventors: Thomas F. McCutchan, Silver Spring; John B. Dame, Rockville, both of Md.

[73] Assignee: The United States of America as represented by the Secretary of the Department of Health and Human Services, Washington, D.C.

[21] Appl. No.: 636,261

[22] Filed: Jul. 31, 1984

[51] Int. Cl.[4] ...................... C12P 19/34; C12N 15/00; C07H 15/12

[52] U.S. Cl. .................................. 435/91; 435/172.3; 935/9; 935/11; 536/27

[58] Field of Search .................. 435/172.3, 91, 68, 70; 536/27; 935/9, 15, 6

[56] References Cited

U.S. PATENT DOCUMENTS 4,237,224 12/1980 Cohen et al. .......................... 435/68
4,399,216 8/1983 Axel et al. ............................. 435/6
4,554,250 11/1985 McCullough et al. ............. 435/172

OTHER PUBLICATIONS

Doctor et al, In *Methods in Enzymology*, vol. XXIX, Chapter 29, pp. 419–431, 1974, Academic Press, Inc.
Maniatis et al., In *Molecules Cloning: A Laboratory Manual*, pp. 140–141, 270–294, 1982, Cold Spring Harbor Laboratory.
Britten et al, In *Methods in Enzymology*, vol. XXIX, Chapter 29, pp. 363–385, 1974, Academic Press, Inc.
McCutchaon et al., Science, vol. 225: 625–628, 1984.
A Microchemical Facility for the Analysis and Synthesis of Genes and Proteins, M. Hunkappiler, S. Kent, M. Caruthers, W. Dreyer, J. Firca, C. Giffin, S. Horvath, T. Humkapiller, P. Tempst & L. Hood Nature, vol. 310, Jul. 12, 1984, Division of Biology, California Institute of Technology, Pasadena, CA, 91125.

Primary Examiner—Thomas G. Wiseman
Assistant Examiner—Thomas D. Mays
Attorney, Agent, or Firm—Holman & Stern

[57] ABSTRACT

The present invention discloses isolated functionally intact whole genes and method of obtaining the same. The method includes treating genomic DNA with mung bean nuclease and formamide under controlled conditions. The invention also discloses cloning of said intact whole genes and a library of such cloned genes or any recombinations thereof. The invention is useful in deriving gene products as m-RNA, S-RNA, t-RNA, polypeptides and the like.

5 Claims, 8 Drawing Figures

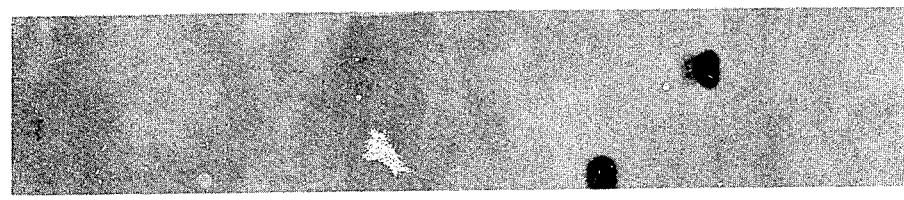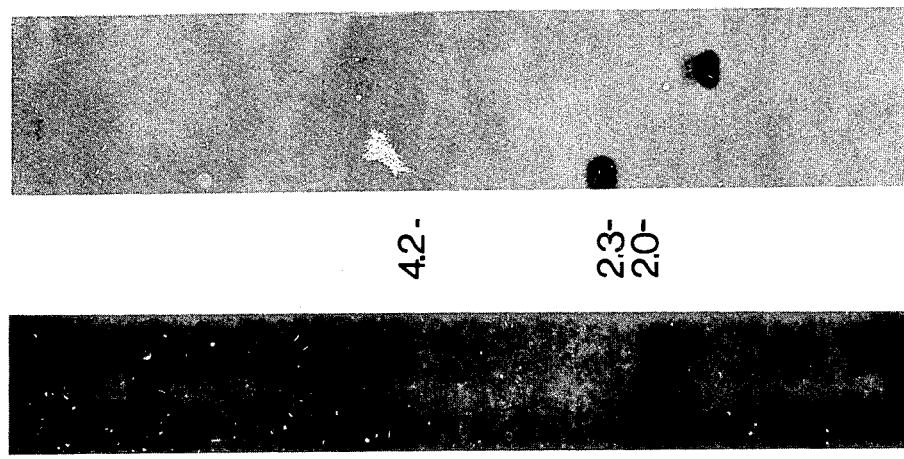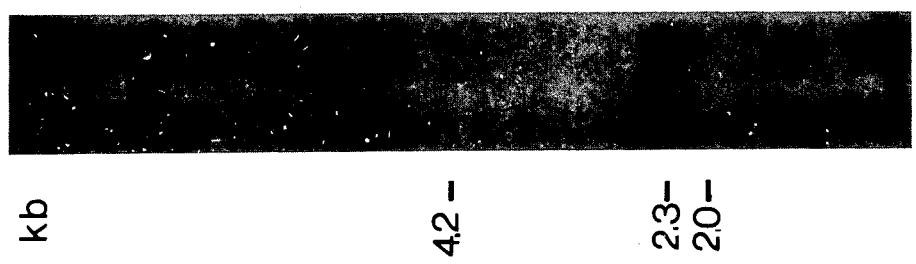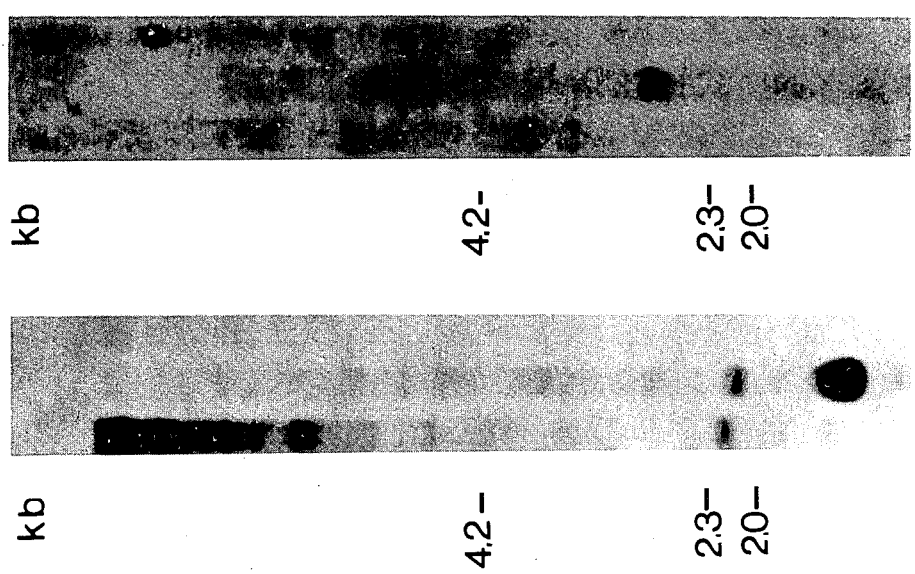

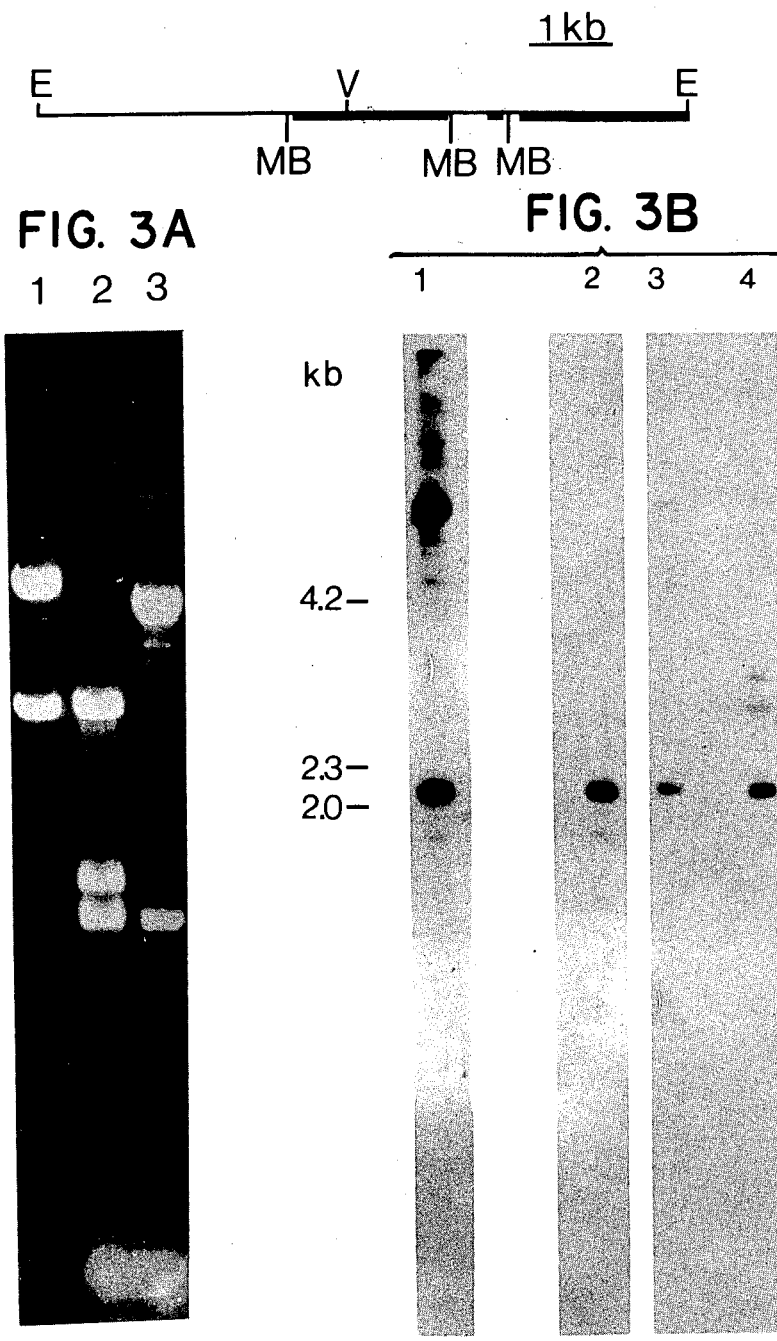

INTACT GENE AND METHOD OF EXCISING AND CLONING SAME

BACKGROUND OF THE INVENTION

1. Technical Field

The present invention is related to obtaining a functionally intact whole gene directly from a genome, said gene being suitable for expression of gene products. The present invention further relates to a method of excising a complete gene from a genome in a single step and cloning the gene thus obtained.

2. Discussion of the Prior Art

Applicants are the first to develop a novel method of obtaining a complete functionally intact gene in a single step, as disclosed herein infra. Hence, there is no prior art known to the Applicants which is directly comparable to the present invention. However, current protocols for cloning genes utilizes one of three methods to prepare DNA for cloning: (1) The preparation of complementary DNA (cDNA) from messenger RNA (i.e., copying the mRNA into DNA); (2) shearing of genomic DNA into randomly broken fragments; and (3) cutting of genomic DNA into reproducible fragments with restriction endonucleases.

Once DNA fragments have been prepared, they are ligated into viral or plasmid vectors where they are reproduced. If the DNA contains a gene which codes for a protein product (most often this is the commercial reason to clone the DNA in the first place), the expression (production) of that protein or some part of it by the clone of interest is used to detect the gene-containing clone. A commonly used method to detect these protein products is binding of antibodies specific for the protein product.

The cDNA technique, which is most commonly used for preparing DNA for cloning, has the following limitations: (1) In almost every case only a part of the gene is cloned; (2) The piece of the cloned gene is usually biased toward the part which codes for the carboxyl terminal end of the protein; (3) The technique depends on a ready supply of mRNA which is only made, in most cases, in certain tissues or life cycle stages which may be difficult to obtain.

The present invention obviates the problems of the cDNA technique by cloning the complete gene in a single step. This reduces the time needed to get the complete gene, which of course, can also be obtained after cDNA cloning, but by going on to the restriction endonuclease method of preparing DNA for cloning and repeating the cloning process. Since the method of detection of a clone may be biased away from the structures displayed in the protein at the carboxyl terminal end, the technique of the present invention, which clones the complete gene, would not be subject to that problem. This could be exemplified by a cell-surface membrane antigen where the immune system only produced antibodies against amino terminal portions of the protein.

Finally, the technique of the present invention prepares DNA fragments containing the genes in direct proportion to the number of copies of that gene in the genome rather than to the relative amount of mRNA present in the biological sample available. This advantage overcomes the problem of cloning a gene for a protein which is present in only limited quantity or which is produced in only tiny amounts by a cell sample and which can be detected only by sensitive detection methods. This is so because the mRNA to make the cDNA for the gene of interest is normally present only in cells where the protein is made.

The other two commonly used techniques may not have the disadvantages of the cDNA technique, but in turn have disadvantages of their own. The random shear method does not suffer from the lack of mRNA, but like the cDNA technique most often results in the cloning of only a portion of the gene. Also due to the small sizes of the pieces of DNA used in this method a larger number of clones must be examined to find the gene.

The restriction endonuclease method of preparing DNA for cloning is usually a required second step for the cDNA and for random shear techniques to eventually clone the entire gene. It also may be used to clone genes directly, but has the disadvantage that numerous restriction enzymes must be tried to find just one (of ~100) enzyme, which will cut the DNA in the right position to yield the gene or a portion of it in a form which the cloning vector can allow to be expressed. The reason for this is that a restriction enzyme inherently recognizes a specific 4 or 6 base pair sequence of the DNA and cuts the genomic DNA everywhere the recognition sequence is present. Since the DNA base sequence is stable, the position of these sites is fixed. For many genes it may be difficult or impossible to find the appropriate enzyme to cut the gene containing DNA fragment in a form allowing the gene product to be expressed.

The present invention provides advantages over the prior art techniques by first cutting the DNA at specific sites, less than 100 bases from the front and the rear of the coding area of the gene. It does not cut randomly within the gene. This results in DNA pieces containing the whole gene as opposed to fragments or small portions of a gene. The frequency of the appropriate DNA fragment in the clone mixture is dependent on gene copy number and the size of the DNA of the genome rather than the amount of mRNA available. Furthermore, the close proximity of the cut site to the start of the gene makes the DNA suitable for expression of the gene product in many expression vectors. Moreover, the cut is not specific for a certain base sequence, rather it recognizes a structure in the DNA and cuts somewhat randomly within a certain base stretch overcoming the problem present in many expression vectors of the DNA being in the right reading frame to allow the gene product to be expressed. The present invention is useful both for prokaryotic as well as eukaryotic genomes, hence is of general applicability.

SUMMARY OF THE INVENTION

It is, therefore, an object of the present invention to obtain an isolated, functionally intact whole gene.

It is a further object of the present invention to clone the isolated complete gene.

It is another object of the present invention to provide a bank or library of intact whole genes or gene fragments derived form said intact whole genes or reconstructed recombinant variations thereof.

It is a still further object of the present invention to obtain useful macromolecules including gene products from the cloned whole gene.

Another object of the present invention is to provide a method of obtaining intact whole gene in a single step process of treating the genomic DNA with a mixture comprising a nuclease and denaturing agent.

Other objects and advantages will become apparent as the description of the present invention proceeds.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 1 shows an analysis of DNA fragments released from genomic DNA by mung bean nuclease digestion. Plasmodium or rhesus monkey DNA (one $\mu$g) was digested with mung bean nuclease in varying amounts of formamide. *P. falciparum* and *P. lophurae* DNA digestions were done in 30-40% formamide. The DNA was then electrophoresed through 0.8% agarose for 22 hrs at 2 v/cm in an Aguebog apparatus Model 850 (Aguebog Machine Shop, Aguebog, N.Y.), transferred to nitrocellulose and hybridized with a radiolabelled probe. FIG. 1A Southern blots were hybridized to a radiolabelled fragment of a plasmid, pA1, containing a chicken $\beta$-actin gene. (1) *P. knowlesi* DNA in 40% formamide. (2) *P. knowlesi* DNA in 45% formamide. (3) Rhesus DNA in 45% formamide. FIG. 1B A Southern blot hybridized to a radiolabelled DNA plasmid probe, $\beta$37, containing the $\beta$-tubulin gene from Chlamydomonas. (1) *P. knowlesi* DNA in 40% formamide. (2) *P. knowlesi* DNA in 45% formamide. (3) Rhesus DNA in 45% formamide. FIG. 1C A Southern blot hybridized to a radiolabelled oligonucleotide homologous to the histidine rich protein of *P. lophurae*. (1) *P. lophurae* DNA in 30% formamide. (2) *P. lophurae* DNA in 35% formamide. FIG. 1D A Southern blot hybridized to a plasmid pmPf5 containing the complete coding region of the circumsporozite gene of *P. falciparum*. (1) *P. falciparum* DNA in 35% formamide. (2) *P. falciparum* DNA in 40% formamide.

FIG. 3 is a map of the plasmid pPbSL7.8 insert and shows restriction sites as well as 3 mung bean clevage sites which occur in restrictions containing 45% formamide. The thick lines represent, from left to right, the coding area for the small rRNA, the 5.8S RNA and 2.2 kb of the large rRNA of *P. berghei*. FIG. 3A Mung bean nuclease sites in a cloned fragment of the ribosomal gene of *P. berghei*. 0.5 $\mu$g aliquots of pPbSL7.8 DNA were treated with EcoR1 (lane 1), mung bean nuclease and EcoR1 sequentially (lane 2) or mung bean nuclease alone (lane 3). Products from reactions were then electrophoresed through 1.2% agarose at 2 v/cm for 18 hrs, and the DNA visualized by staining with ethidium bromide. FIG. 3B The comparision of digestion products resulting from mung bean cleavage of cloned and genomic DNA. DNA from pPbSL7.8 (lane 1), and $\lambda$Pb27 (lane 2) were digested with mung bean nuclease as described herein. Genomic DNA (5 $\mu$g) was digested with mung bean nuclease in 40% (lane 3) or 45% (lane 4) formamide. The products were compared by Southern blot analysis using a radiolabelled plasmid (pPbSL5.6) probe which contains only the gene for the small rRNA subunit. The band at 6.7 kb in lane 1 results from hybridization of the probe to a pBr322 derived sequence on the blot.

DETAILED DESCRIPTION OF THE INVENTION

Figure 2:
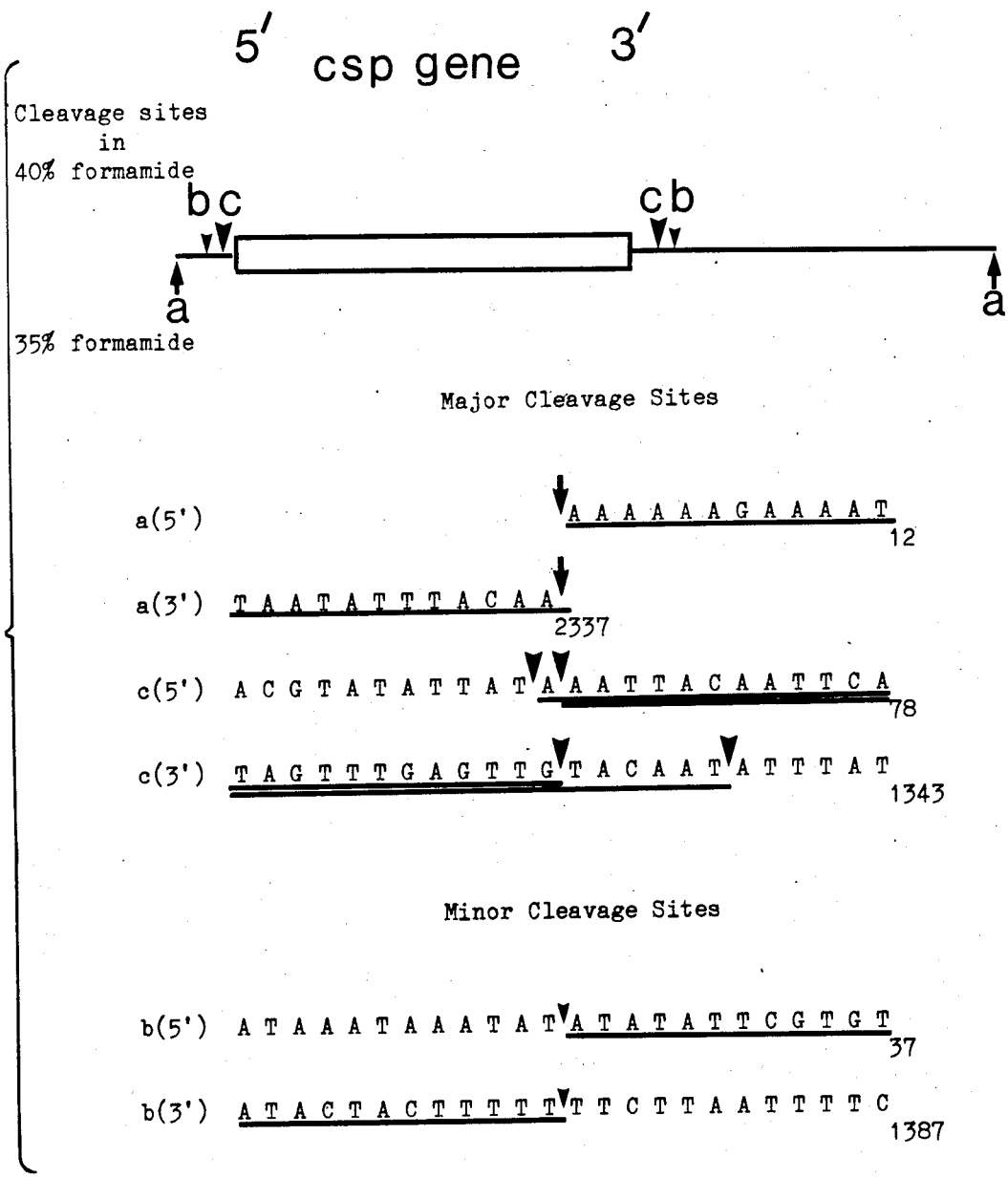
FIG. 2 shows a map of mung bean cleavage sites in the *P. falciparum* circumsporozoite protein (CSP) gene. The coding region is boxed; noncoding regions are represented by a line. Cleavage sites in 35% formamide, a, are represented by arrows. The predominant cleavage sites in 40% formamide, c, are represented by large darts. Minor cleavage sites in 40% formamide, b, are represented by small darts. A bacteriophage $\lambda$library containing mung bean treated *P. falciparum* DNA inserts was constructed as described infra in the vector $\lambda$gt11. Clones containing the circumsporozoite protein gene were selected by immunoscreening using a monoclonal antibody. The primary sequence of DNA to both sides of the termini of several clones is shown. The number after each line of sequence indicates the position of this nucleotide in the total sequence of the circumsporozoite protein gene. The underlined part of the sequence was derived by sequence analysis of the termini of clones. a, pmPf1; b, pmPf15; c, pmPf5, pmPf8 and pmPf13.

These and other objects and advantages are achieved by the present invention which comprises an isolated, functionally intact whole gene and a method of isolating a functionally intact whole gene comprising treating a source of said gene with an amount of a single strand nuclease and a denaturing agent sufficient for releasing said gene from said source.

Any source containing genes can be employed for the practice of this invention. Genomes or genomic DNA are examples of the source material from which said intact genes can be obtained. DNA from which intact genes can be obtained may either be from prokaryotic or eukaryotic organisms, native or recombinant, natural or synthetic or of any other type so long as it has intact genes present therein.

Suitable nuclease which can be employed is single strand nuclease such as mung bean nuclease which is commercially available, for example from Pharmacia P-L Biochemicals, Piscataway, N.J. The enzyme is used in an amount sufficient to excise the DNA, for example 1 unit of enzyme per 1 $\mu$g of DNA. But the amount may vary from 0.5 unit to 2 units or the like depending on the reaction conditions. The enzyme unit is that as defined by the supplier, e.g. Pharmacia P-L Biochemicals.

Other nucleases which could be used are those described in "Nucleases" Ed. Linn & Roberts, Cold Spring Harbor, N.Y. 1982, which is incorporated herein by reference, of particular interest being an article therein entitled "Single Strand Specific Nucleases" by Shishido and Ando at page 167 et seq.

Suitable denaturing agents which could be employed in the practice of the present invention are preferably amides, particularly formamide in a concentrating range of about 5% to 65% (v/v) of formamide in the reaction mixture. Examples of other denaturing agents are dimethyl sulfoxide, dimethyl formamide and formaldehyde in an amount up to 50%, 30% and 2%, respectively. A description of suitable denaturing agents can be found in *Wells et al.*, Prog. Nucl. Acid Res. Mol. Biol. 24,167, 1980 which is incorporated herein by reference.

The reaction mixture is a buffer solution having a pH of about 4.2-4.8. A preferred buffer solution. comprises about 0.2M NaCl, 1mM ZnSO$_4$ and 30 mM Na-acetate, pH 4.6.

The term gene or expression product includes such entities as messenger, transfer, soluble and ribosomal ribonucleic acids, peptide, poly-peptide or proteins and antibodies made against said peptide or protein.

Included within the scope of the present invention are also partial fragments, recombinants, or any other form of reconstructed or reconstituted entities derived from the isolated intact gene obtained in accordance with the present invention.

Typically mung bean nuclease reaction is carried out in a volume of 100 μl with 1 unit of enzyme per 1 μg of genomic DNA at about 50° C. in varying concentrations of formamide, preferably about 20%–50% (v/v) for about 20–40 minutes in 0.2M NaCl, 1 mM ZnSO$_4$ and 30 mM Na-acetate, pH 4.6. The incubation is carried out for a sufficent time, usually about 30 minutes in the above reaction mixture. Then, the solution is diluted 4-fold with about 0.01M ethylenediamine tetraacetate (EDTA) and extracted with phenol as is well known in the art. DNA fragments containing the desired intact whole genes are then isolated from this reaction mixture by precipitating said DNA fragments with 2 volumes of absolute ethanol. The precipitate is left overnight at −20° C., then centrifuged at about 10,000 rpm (12,000g) for about 30 minutes in a refrigerated centrifuge. The residue comprising the isolated intact gene(s) is rinsed with 80% ethanol in H$_2$O, the supernatant poured off, the residue re-centrifrized if necessary and then dried in vacuum. The dried DNA representing the intact whole (complete) gene can then either be stored at −20° C. or dissolved in a suitable buffer, e.g. 10mM tris-HCl, pH 7.5 containing 1 mM NaEDTA and used for subsequent steps e.g., cloning, transcription, translation, electrophoresis and the like or for obtaining other gene products or macromolecules (proteins, antibodies, and the like) or stored frozen for later use as desired.

Cloning of isolated whole gene can be accomplished by any suitable technique, such as described by Young and Davis in Proc. Natl. Acad. Sci. USA, 80:1194, 1983 and Science, 222:778, 1983, both of which publications are incorporated herein by reference. Any suitable cloning vehicle, e.g. a microbial or yeast plasmid or a bacteriophage and the like can be employed to clone the whole gene. A preferred cloning vehicle is λgt11.

In order to test for or produce the product(s) coded by the isolated gene, the gene is artificially introduced into an expression vector, preferably a unicellular organism capable of expressing said gene usually in the form of a peptide or protein. The poly-peptide or protein thus expressed is usually identified by standard techniques such as immunological procedures, electrophoresis, aminoacid sequencing and the like. Depending on the importance and significance of the expression product (e.g., protein), scientifically, commercially, pharmaceutically, etc., the expression product can be further used to produce antibodies (mono or polyclonal) or the like, all of which are envisaged within the scope of the present invention.

For analyzing the results of mung bean nuclease digestion under various controlled conditions, standard Southern blot analysis is employed as described by Southern, J. Mol Biol. 98:503, 1975 which is incorporated herein by reference. Both unlabelled or radiolabelled probes can be used.

The term 'functionally intact' means the gene is capable of encoding, controlling or directing all those functions which are inherent in a gene, e.g. transcription, translation and the like.

DESCRIPTION OF THE PREFERRED EMBODIMENTS

All publications or patents mentioned infra are herein incorporated by reference.

As an illustrative example of the present invention, genomic DNA was cleaved with mung bean nuclease under a series of controlled conditions and the gene products analyzed by Southern blot analysis. Cloned genes isolated from Plasmodium and other organisms or synthetic oligonucleotides were used as probes.

Four different DNAs were used as radiolabelled probes for Southern blot analysis, cDNAs for chicken B-actin and Chlamydomonas tubulin were selected because they have been used to find corresponding genes in a broad range of organisms including parasitic protozoa, Cleveland, et al. *Cell* 20, 95 (1980) and Silflow, et al. *Cell* 24, 81 (1981). A series of different cleavage conditions, particularly with respect to different formamide-concentrations were tested. The analysis of the reactions in 40% and 45% formamide are shown in FIG. 1. Southern blot analysis of *Plasmodium knowlesi* DNA after clevage in 45% formamide shows a single predominate fragment at 1.6 kb (kilo-bases) hybridizing to the actin probe (FIG. 1A) and one at 2.6 kb hybridizing to the tubulin probe (FIG 1B). These fragments are of adequate size to encode the corresponding products. The 40% formamide reactions also contain fragments that are homologous to the probe but are larger.

Investigation of the area surrounding the histidine-rich protein (HRP) of *Plasmodium lophurae*, by Kilejian. *J. Biol. Chem.* 249, 4650 (1974), was done using a radiolabelled oligonucleotide consisting of a sequence of five tandem histidine codon triplets as described by Wallach *Proc. Natl. Acad. Sci. USA* 80, 1867 (1983). DNA from *P. lophurae* (greater than 95% pure) was digested with mung bean nuclease in 30%, 35% and 40% formamide. Analysis of the 30% and 35% reactions showed a band at 2.2 kb (FIG. 1C). This is the same size as the mRNA described by Wallach *Proc. Natl. Acad. Sci. USA* 80, 1867 (1983) which codes for the HRP and hybridizes to the oligonucleotide probe. Again the mung bean nuclease excises a gene-sized fragment.

The circumsporozoite protein gene was investigated using clone pmPf5 as a probe, which contains the complete coding area of the gene as described by Dame et al. in *Science*, Aug. 10, 1984, which publication in its entirety is incorporated herein by reference. In Southern blots only one band at 2.3 kb was seen in the 35% formamide reaction. One major band of 1.3 kb and one minor species of slightly larger size were seen in the 40% formamide reaction. All these three fragments were then cloned. Sequence data on these have been described, infra and in Dame et al, supra.

To determine the site of mung bean nuclease cleavage, fragments generated by mung bean nuclease digestion were cloned and sequenced. This was accomplished by combining equal aliquots of DNA from 35% and 40% formamide mung bean nuclease reactions shown in FIG. 1D and ligating them into the expression vector, λgt11. Two hundred thousand inserts containing clones were immunologically screened with monoclonal antibodies specific for the circumsporozoite protein of *P. falciparum* (Dame et al, supra). Seven of thirty-five positive clones were analyzed in detail. The fragments detected by Southern blot analysis in FIG. 1D were all found in this group. Three clones contained a 2.3 kb fragment (35% formamide reaction, lane 1). Three contained a 1.3 kb fragment and one contained a 1.35 kb fragment (40% formamide reaction, lane 2). The DNA sequence of the 2.3 kb fragment was then determined (Dame et al, supra). The 2.3 kb fragment from the 35% formamide reaction has a site about 80 bp 5' to the start of the gene and a site approximately one thousand bp 3' to the gene. Both the 5' and 3' termini of other clones were sequenced and compared to the sequence of the 2.3 kb fragment (FIG. 2). The three 1.3 kb fragments have sites either 10 or 11 bp from the start of the gene and sites either 27 or 35 bp from the 3' end of the gene. One clone has been sequenced which contains a minor fragment 1.35 kb from the 40% formamide reaction. This fragment is cut 52 bp in front of the gene and 60 bp after it. Sequences at the termini of these clones represent sequences spared by the nuclease (FIG. 2). There is no apparent sequence homology either 5' and 3' to cuts. Although the cut sites are dA.dT rich, they have no more dA.dT than surrounding areas both in and outside the gene that are not cut. Further, the 5' to a given site is no more dA.dT rich than the sequence 3' to a site.

It should be noted that cleavage depends on the structure of the naked DNA. A cloned DNA sequence synthesized in and isolated from *E. coli* yields the same cleavage products as genomic DNA from Plasmodium. Mung bean nuclease cleavage of cloned Plasmodium ribosomal genes in formamide yields fragments of defined size which correspond to the coding areas for the small ribosomal RNA, the 5.8S RNA and the large ribosomal RNA. FIG. 3 shows a map of a cloned plasmid, pPbSL7.8, which contains an EcoRl DNA fragment from *P. berghei* with the coding region for the entire small rRNA, the 5.8S RNA and 2.2 kb of the large ribosomal gene which is interrupted by an EcoRl cleavage site. The data in FIG. 3A show the products of cleavage of the cloned restriction fragment with either a restriction nuclease or mung bean nuclease. Mung bean nuclease cleavage products of cloned ribosomal genes are directly compared with those from total DNA in FIG. 3B. The major Plasmodium derived fragments are all the same size. This suggests that mung bean nuclease cuts these cloned Plasmodium DNAs nearly quantitatively and yields the same products as genomic DNA. The fact that both cloned and genomic DNAs react identically indicates that the DNA has not been previously cut by Plasmodium nucleases. Therefore, cleavage depends on the structure of the DNA clone. DNA from other organisms were also analyzed. Cleavage that yields fragments of defined size was not uncommon even in DNA from higher eukaryotic organisms (FIG. 1A, lane 3). Some DNAs, like that of the parasitic trematode *Schisotosoma mansoni*, yielded single, small fragments that hybridized either to actin or tubulin probes. This indicates broader utility of the present invention.

Isolated intact genes in accordance with the present invention can, of course, be preserved as a gene-bank or library. An exemplary λgtll library is constructed as follows. Plasmodium DNA (5–10 μg) is digested with mung bean nuclease as described herein in 30%, 35%, 40% or 45% formamide. The reaction product from each of the four reactions is diluted four-fold with 0.01M EDTA, phenolized and precipitated in 2.5 volumes of ethanol. An aliquot of each DNA is analyzed by Southern blot analysis using a DNA probe homologous to either actin or tubulin. The DNA from the reactions containing 'gene sized' fragments homologous to the probe are combined and used as a source of fragments to ligate into λgtll. 35%. and 40% formamide reaction products for *P. falciparum* libraries are combined. In this case the DNA was treated with Klenow fragment but in the production of other libraries, this step can be eliminated. EcoRl linkers (BRL) are blunt-end ligated to the treated fragments. After digestion with EcoRl, free linkers are separated from larger fragments using a 1.5×20 cm Sepharose 4B column. λgtll is self-ligated and digested with EcoRl. The *P. falciparum* fragments are ligated to the prepared λgtll overnight at 12° C. with T4 DNA ligase (BRL) under the conditions recommended by the supplier. The ligation reaction products are packaged into infectious phage in vitro (Promega Biotec). From an initial 3 μg of starting genomic DNA, $4 \times 10^5$ packaging events are scored by detectable interruption of the B-galactosidase gene of λgtll on RY1090 growing on LB agar supplemented with Xgal and IPTG. A DNA library of *P. knowlesi* has also been made in this fashion except that the products of mung bean nuclease cleavage in 40% and 45% formamide are used.

One of the benefits of the present invention is that recombinant libraries can be produced containing mostly complete gene fragments. The presentation of any gene in the library then relates directly to its copy number in the genome. This is of special importance with regard to those conditions where proteins of importance are not easily available because such proteins are produced during a particular stage in the life cycle of an organism or are not available in sufficient quantity.

Isolation of intact genes, cloning thereof and producing protein from cloned isolated gene and using the protein to produce antibodies (mono or polyclonal), all of which are now made possible by the present invention, opens a new vista in bio-technology. Such was not heretofore possible for the simple reason that intact functional genes could not be isolated directly from genome in a simple, efficient, single step reaction.

The fact that the mung bean nuclease technique has been found to be successful in obtaining functionally intact complete isolated genes from such organisms as Plasmodium, *Schistosoma mansoni* and *Vibrio cholerae* in accordance with the present invention, indicates that the phenomenon is general and not an isolated one.

It is understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A process for excising from a genomic DNA a complete sequence for encoding a protein which comprises treating a genomic DNA susceptible to mung bean nuclease and formamide under controlled conditions in a reaction mixture comprising mung bean nuclease and formamide in an amount sufficient for excising in a single step, directly form the genomic DNA, a complete nucleotide sequence encoding a protein when said nucleotide sequence is cloned in a foreign expression vector, said excised nocleotide sequence having therein protein initiation and termination codons.

2. The process of claim 1 wherein the amount of nuclease ranges from about 0.5 to about 2 units of the nuclease per μg of DNA.

3. The process of claim 2 wherein the amount of formamide ranges from about 5% to about 65% by volume of the reaction mixture.

4. The process of claim 3 wherein the amount of nuclease is 1 unit and formamide ranges from about 30% to about 45%.

5. The process of claim 4 treating said DNA at about 50° C. for about 30 minutes in a buffer solution at a pH of about 4.6 and isolating said gene from the reaction mixture.

* * * * *